US008568368B2

(12) United States Patent
Lampropoulos et al.

(10) Patent No.: US 8,568,368 B2
(45) Date of Patent: Oct. 29, 2013

(54) CONTRAST MEDIA DIFFUSION SYSTEM

(75) Inventors: Fred P. Lampropoulos, Salt Lake City, UT (US); Kenneth H. Carter, Fruit Heights, UT (US); Roger W. Christensen, Sandy, UT (US); Gar Hendry, Salt Lake City, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 266 days.

(21) Appl. No.: 12/102,711

(22) Filed: Apr. 14, 2008

(65) Prior Publication Data
US 2009/0259199 A1 Oct. 15, 2009

(51) Int. Cl.
*A61M 5/00* (2006.01)

(52) U.S. Cl.
USPC .......................................... 604/246; 604/248

(58) Field of Classification Search
USPC .................................................. 604/246–249
See application file for complete search history.

(56) References Cited

U.S. PATENT DOCUMENTS

| 337,249 | A | | 3/1886 | Conkle |
|---|---|---|---|---|
| 2,051,247 | A | | 8/1936 | Haes |
| 3,683,929 | A | | 8/1972 | Holter |
| 3,949,745 | A | | 4/1976 | Howell |
| 4,055,176 | A | | 10/1977 | Lundquist |
| 4,294,288 | A | | 10/1981 | Murthy |
| 4,332,247 | A | * | 6/1982 | Mittleman et al. ............. 604/82 |
| 4,769,012 | A | | 9/1988 | Quang et al. |
| 5,234,414 | A | | 8/1993 | Hung |
| 5,372,591 | A | | 12/1994 | Jeng et al. |
| 5,415,325 | A | | 5/1995 | Shu |
| 5,423,346 | A | | 6/1995 | Daoud |
| 5,505,707 | A | | 4/1996 | Manzie et al. |
| 5,569,208 | A | | 10/1996 | Woelpper et al. |
| 5,575,779 | A | | 11/1996 | Barry |
| 5,776,109 | A | | 7/1998 | Urrutia |
| 5,868,715 | A | | 2/1999 | Tung |
| 5,970,935 | A | | 10/1999 | Harvey et al. |
| 6,213,986 | B1 | | 4/2001 | Darling, Jr. |
| 6,261,267 | B1 | | 7/2001 | Chen |
| 6,500,156 | B1 | | 12/2002 | Stansbury |

(Continued)

OTHER PUBLICATIONS

Notification of Transmittal of the International Search Report and the Written Opinion of the International Searching Authority issued Jun. 3, 2009 in International Application No. PCT/US2009/039484.

(Continued)

*Primary Examiner* — Kevin C Sirmons
*Assistant Examiner* — Brandy S Lee
(74) *Attorney, Agent, or Firm* — Stoel Rives LLP

(57) ABSTRACT

A contrast media delivery system having a flow regulator assembly that allows a practitioner to regulate the passage of contrast media into a burette while minimizing turbulence and the formation of microbubbles in the contrast media. The flow regulator assembly can be actuated by twisting a rotatable cap. When the rotatable cap is released, the flow of contrast media from the inlet to the burette is stopped. A diffuser having a contact surface is provided which disperses contrast media as it passes into the burette to ensure that the contrast media flows smoothly and uniformly down the wall of the burette and into the volume of contrast media. A float and seating assembly which provides optimal sealing of the outlet of the burette while also allowing separation of the float from the seat when the burette is being refilled with contrast media.

17 Claims, 11 Drawing Sheets

(56) References Cited

U.S. PATENT DOCUMENTS

| | | | |
|---|---|---|---|
| 6,695,004 B1 | 2/2004 | Raybuck | |
| 7,731,699 B2 | 6/2010 | Mottola | |
| 2002/0115965 A1 | 8/2002 | Jang et al. | |
| 2005/0113766 A1 | 5/2005 | Mottola | |
| 2006/0129111 A1 | 6/2006 | Mottola | |
| 2006/0264850 A1* | 11/2006 | Mottola | 604/254 |
| 2007/0106228 A1* | 5/2007 | Bell et al. | 604/247 |

OTHER PUBLICATIONS

Notice of Abandonment issued Jul. 20, 2009 in co-pending U.S. Appl. No. 10/724,427.
Office Action issued Jan. 12, 2009 in co-pending U.S. Appl. No. 10/724,427.
Response to Notice of Non-Compliant Amendment filed Jan. 5, 2009 in co-pending U.S. Appl. No. 10/724,427.
RCE and Amendment and Response filed Dec. 3, 2008 in co-pending U.S. Appl. No. 10/724,427.
Notice of Non-Compliant Amendment issued Dec. 5, 2008 in co-pending U.S. Appl. No. 10/724,427.
Final Office Action issued Jun. 3, 2008 in co-pending U.S. Appl. No. 10/724,427.
Amendment and Response filed Mar. 7, 2008 in co-pending U.S. Appl. No. 10/724,427.
Office Action issued Sep. 7, 2007 in co-pending U.S. Appl. No. 10/724,427.
Response to Restriction Requirement filed Aug. 13, 2007 in co-pending U.S. Appl. No. 10/724,427.
Restriction Requirement issued Jun. 13, 2007 in co-pending U.S. Appl. No. 10/724,427.
Preliminary Amendment filed Jun. 19, 2006 in co-pending U.S. Appl. No. 11/008,311.
Interview Summary issued Jul. 15, 2009 in co-pending U.S. Appl. No. 11/008,311.
Office Action issued Feb. 27, 2009 in co-pending U.S. Appl. No. 11/008,311.
Amendment and Response to Office Action filed Aug. 27, 2009 in co-pending U.S. Appl. No. 11/008,311.
Notice of Allowance issued Nov. 30, 2009 in co-pending U.S. Appl. No. 11/008,311.
Request for Continued Examination filed Mar. 1, 2010 in co-pending U.S. Appl. No. 11/008,311.
Preliminary Amendment filed Jul. 27, 2006 in co-pending U.S. Appl. No. 11/424,225.
Office Action issued Nov. 25, 2009 in co-pending U.S. Appl. No. 11/424,225.
Notice of Allowance dated Apr. 15, 2010 for U.S. Appl. No. 11/008,311.
Office Action dated Jun. 15, 2010 for U.S. Appl. No. 11/424,225.
Notice of Allowance dated Oct. 5, 2010 in U.S. Appl. No. 11/424,225.

* cited by examiner

CONTRAST MEDIA DIFFUSION SYSTEM

BACKGROUND OF THE INVENTION

1. Field of the Invention

The present invention relates to contrast media delivery systems. In more particular, the present invention relates to a contrast media delivery system having a flow regulator assembly, diffuser and an improved seat and float assembly which enables the user to simply and efficiently control the flow of contrast media while also minimizing turbulence in a volume of contrast media contained within the system.

2. Relevant Technology

Patient fluid delivery systems have long been used in medicine to ensure safe and reliable delivery of fluids to patients. Typically, such delivery systems include a source of fluid, such as an infusate bag or bottle, a patient access apparatus, such as a catheter or trocar, and delivery tubing for conveying the fluid from the source of fluid to the patient. Some delivery systems also incorporate a burette at one or more positions in the delivery tubing. A burette typically comprises a clear cylindrical apparatus having a chamber of a larger diameter than the delivery tubing. The chamber of the burette is configured to be partially filled with fluid while fluid is flowing to the burette. The chamber of the burette helps eliminate any potential air bubbles in the delivery line. Air bubbles in the delivery line are dissipated as the fluid enters the burette and forms droplets. Additionally, the reservoir of fluid in the burette prevents air from entering into the outlet line of the burette when the flow of fluid from the fluid source to the burette is interrupted.

When the fluid in the fluid source is exhausted, fluid is no longer delivered to the burette from the inlet tubing. Because fluid is no longer delivered to the burette, the fluid level in the burette begins to lower. This allows the practitioner to observe the fluid level in the burette to ascertain whether a replacement fluid source is needed without actually observing the fluid level in the fluid source. As long as the volume of fluid in the burette exceeds a certain threshold, fluid continues to be delivered to the patient from the outlet of the burette. As a result, the burette provides an amount of time in which fluid continues to be delivered to the patient after the fluid source has been depleted. This allows the practitioner to replace the fluid source without interrupting the delivery of fluid to the patient and minimizes the chance for air to be introduced into the fluid path below the burette.

One problem that has been encountered with the use of burettes relates to filling of the chamber of the burette. Typically as the chamber is filled, fluid flowing into the chamber does not immediately contact the volume of fluid in the chamber because the chamber is only partially filled with fluid. Instead, the fluid forms droplets which fall from the burette inlet onto the surface of the fluid volume in the chamber. In some circumstances, when the droplets hit the fluid volume, the velocity of the droplets may create turbulence or microbubbles in the volume of fluid. The formation of microbubbles may be undesirable where the microbubbles may be delivered to the vasculature of the patient.

The formation of microbubbles can be particularly challenging where the fluid being delivered to the patient comprises contrast media. Contrast media is utilized to allow a practitioner to utilize imaging technology such as X-ray or MRI to view the flow of fluids in the patient's vasculature or other body systems. Contrast media typically includes radioactive or isotopic qualities that permit the contrast media to be detected by the imaging equipment. The types of materials that are utilized as contrast media often have a high molecular weight and/or a high viscosity. The high viscosity of contrast media can increase the number and size of microbubbles while also inhibiting the migration of the microbubbles out of the volume of contrast media.

A variety of mechanisms have been developed to minimize the formation of microbubbles in contrast media contained within a burette. One mechanism comprises a ball or other spherical member that is configured to float in the volume of fluid in the burette. The size and buoyancy of the ball is configured such that the droplets strike the surface of the ball instead of the surface of the volume of fluid. This not only slows the velocity of the droplets, but also provides a surface along which the droplets can flow and enter the volume of fluid. Additionally, when the burette is emptied, the ball is configured to provide an air tight seal with the outlet of the burette to prevent air entering the line downstream from the burette when the fluid level reaches the bottom of the burette. By preventing air from entering into the line downstream from the burette, the practitioner does not need to remove air from the line before resuming the flow of fluids to the patient. This allows for smooth and efficient replacement of the fluid source while also resuming the flow of fluid to the patient once the fluid level in the chamber of the burette is returned to normal levels.

One problem that is presented by the configuration of burette float and seat assemblies relates to the air tight seal created between the float and the seat and the related vacuum effect which helps to maintain the air tight seal. The air tight seal and vacuum effect discourages separation of the float from the seat as the drip chamber begins to refill with fluid. Difficulty in separating the float from the seat can occur when the seat is formed from the inner circumference of the chamber. Where the seat is formed from the inner wall of the chamber, the contact between the seat and the float is continuous along much of the bottom surface of the float. As a result, the contact between the seat and the bottom surface of the float can render it difficult for contrast media to flow to the underside of the float. Because buoyancy is created from contact between the contrast media and the underside of the float, insufficient buoyancy is created to overcome the vacuum effect and separation between the float and the seat is inhibited. Additionally, because the contrast media is primarily in contact with the upper surface of the float, downward pressure is exerted on the float by the contrast media. The downward force exerted by the contrast media on the upper surface of the float also prevents separation between the float and the seat.

While the float remains in air tight contact with the seat, flow of contrast media to the patient will not resume. To overcome the vacuum effect and air tight seal between the float and the seat and in attempt to resume the flow of contrast media to the patient, a practitioner may shake or tap the burette in an attempt to dislodge the float. However, shaking or tapping of the burette can result in turbulence in the contrast media and the inadvertent introduction of microbubbles into the contrast media.

Another deficiency of the burette configuration of existing contrast media delivery systems results from the passage of droplets from the inlet of the burette to the volume of contrast media in the burette. In a typical system, when the contrast media enters the burette, it falls from the inlet of the burette until it strikes the surface of the float or the surface of the volume of contrast media. While the float can be configured to be positioned below the inlet of the burette, at least some of the droplets of contrast media can miss the float and directly strike the surface of the volume of contrast media. The falling droplets can result in the formation of turbulence and or microbubbles in the volume of contrast media.

BRIEF SUMMARY OF THE INVENTION

Exemplary embodiments of the invention are directed to a contrast media delivery system having a flow regulator assembly that facilitates the passage of contrast media into a burette while minimizing turbulence and the formation of microbubbles in the contrast media. In one embodiment of the present invention, the flow regulator assembly allows a practitioner to simply and efficiently monitor and control the amount and flow of fluid passing into the burette. For example, the flow regulator assembly can be actuated by twisting or exerting a rotational force on one or more components of the flow regulator assembly. When a user twists or exerts rotational forces on one or more components of the flow regulator assembly, passage of fluid from the inlet of the burette to the volume of contrast media in the burette is permitted. When the user releases the one or more components of the flow regulator assembly such that the flow regulator assembly is no longer subject to rotational force, the flow regulator assembly automatically return to its original position. When the flow regulator assembly returns to its original position, the flow regulator assembly automatically stops the flow of contrast media from the inlet to the burette.

According to another embodiment of the present invention, a diffuser is utilized in connection with the contrast media delivery system. For example, in one embodiment, the diffuser is a component of the flow regulator assembly. The diffuser minimizes micro-bubbles or turbulence that can be formed by contrast media flowing into the burette. The diffuser provides a contact surface for dispersing contrast media as it passes into the burette. The contact surface of the diffuser ensures that contrast media passes to the wall of the burette such that the contrast media flows smoothly and uniformly down the wall of the burette and into the volume of contrast media, minimizing the formation of turbulence or micro-bubbles in the volume of contrast media.

According to another embodiment of the present invention, a float and seating assembly is provided in connection with the contrast media delivery system. For example, in one embodiment the float and seating assembly provides optimal sealing of the outlet of the burette while also allowing separation of the float from the seat when the burette is being refilled with contrast media. The seating assembly can include a seat and a plurality of projections. The seat is raised relative to the bottom of burette such that a volume of fluid is positioned between the float and the bottom of the burette when the float is resting on the seat. In this manner, the volume of fluid positioned between the float and the bottom of the burette can provide sufficient buoyant force to separate the float from the seat and allow the passage of fluid into the outlet of the burette when the burette begins to refill with contrast media. In one embodiment, the plurality of projections are associated with one or more fluid passageways which allow the contrast media to contact the underside of the float. Additionally, the projections can guide the float to a desired position on the seat as the fluid level in the burette lowers.

DETAILED DESCRIPTION

Figure 1:
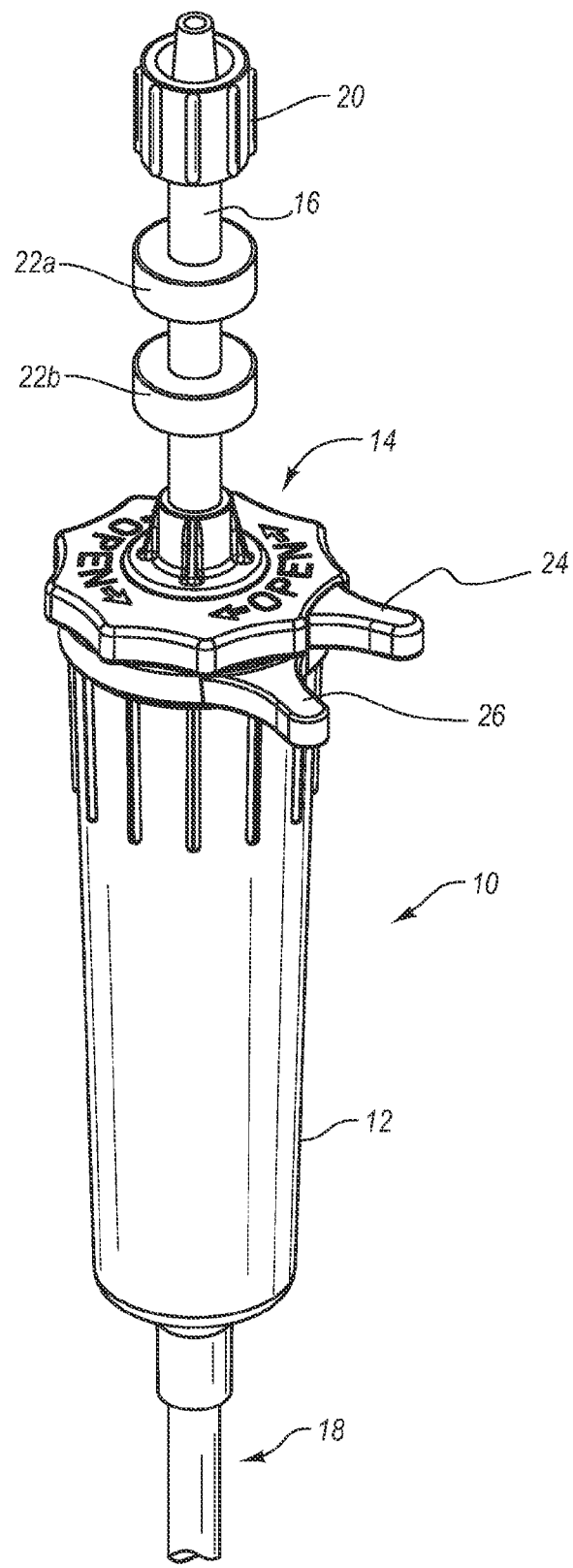
FIG. 1 is a front perspective view of a contrast media delivery system having a flow regulator assembly according to one exemplary aspect of the present invention.

FIG. 1 is a perspective view of a contrast media delivery system 10 according to one embodiment of the present invention. Contrast media delivery system 10 is utilized to allow a practitioner to deliver a controlled and continuous flow of contrast media from a contrast media source to a desired location within a patient. In the illustrated embodiment, contrast media delivery system 10 comprises a burette 12, a flow regulator assembly 14, an inlet 16, and an outlet 18.

Burette 12 comprises a chamber configured to hold a volume of contrast media. Burette 12 can be comprised of a deformable material, such as a thermoplastic elastomer, such as flexible polyvinyl chloride, which allows a user to squeeze, compress, or otherwise manipulate burette 12 to help initiate the flow of contrast media through contrast media delivery system 10. Burette 12 can also be comprised of a clear or semi-translucent material allowing a practitioner to view the amount of contrast media contained within burette 12.

Flow regulator assembly 14 is positioned on the input end of burette 12. Flow regulator assembly 14 allows a practitioner to simply and efficiently regulate the flow of fluid from inlet 16 to burette 12. In the illustrated embodiment, flow regulator assembly 14 is actuated by twisting one or more components of the flow regulator assembly 14. When a user twists or exerts rotational forces on one or more components of flow regulator assembly 14, passage of fluid from inlet 16 to burette 12 is permitted. When a user releases the one or more components of flow regulator assembly 14 such that the one or more components of flow regulator assembly 14 is no longer subject to rotational force, the components of flow regulator assembly 14 automatically return to their original position. When the components of flow regulator assembly 14 return to their original position, flow regulator assembly 14 automatically stops the flow of contrast media from inlet 16 to burette 12.

In the illustrated embodiment, flow regulator assembly 14 includes a first handle 24 and a second handle 26. When the flow regulator assembly 14 is in a released position as is depicted, first handle 24 and second handle 26 are not in alignment. When flow regulator assembly 14 is in a released position, the free flow of contrast media from inlet 16 to burette 12 is not permitted. To begin the free flow of contrast media, as previously discussed, the user twists flow regulator assembly 14. In the illustrated embodiment, to begin the flow of contrast media, the user manipulates handle 24 in the direction of handle 26. When handle 24 is aligned with handle 26, the free flow of contrast media is permitted. By utilizing a handle 24 in connection with handle 26, the user can simply and reliably identify when the components of flow regulator assembly have been moved to the desired position to allow for the flow of contrast media.

According to one embodiment of the present invention, flow regulator assembly 14 is manipulated by the user during the initial filling of burette 12 with fluid. Flow regulator assembly 14 allows the user to establish and alter the fluid level within burette 12. When the fluid level in burette 14 is established, the contrast media delivery system 10 maintains the level of the contrast media within burette 12 automatically and without requiring additional manipulation of flow regulator assembly 14. According to an alternative embodiment of the present invention, the flow regulator assembly is utilized to control all flow of contrast media within contrast media delivery system 10.

In the illustrated embodiment, inlet 16 is positioned upstream of flow regulator assembly 14 and burette 12. Outlet 18 is coupled to the downstream portion of burette 12. Inlet 16 includes a luer coupler 20 and check valves 22a,b. Luer coupler 20 is utilized to secure contrast media delivery system 10 to a source of contrast media. As will be appreciated by those skilled in the art, a variety of types and configurations of coupling mechanisms can be utilized to secure contrast media delivery system 10 to a source of contrast media including a contrast media delivery bottle, tubing assembly with spike, tubing, an infusate bag, an infusate reservoir, or the like. Check valves 22a and 22b ensure that contrast media is flowing only in the direction toward burette 12.

Figure 2A:
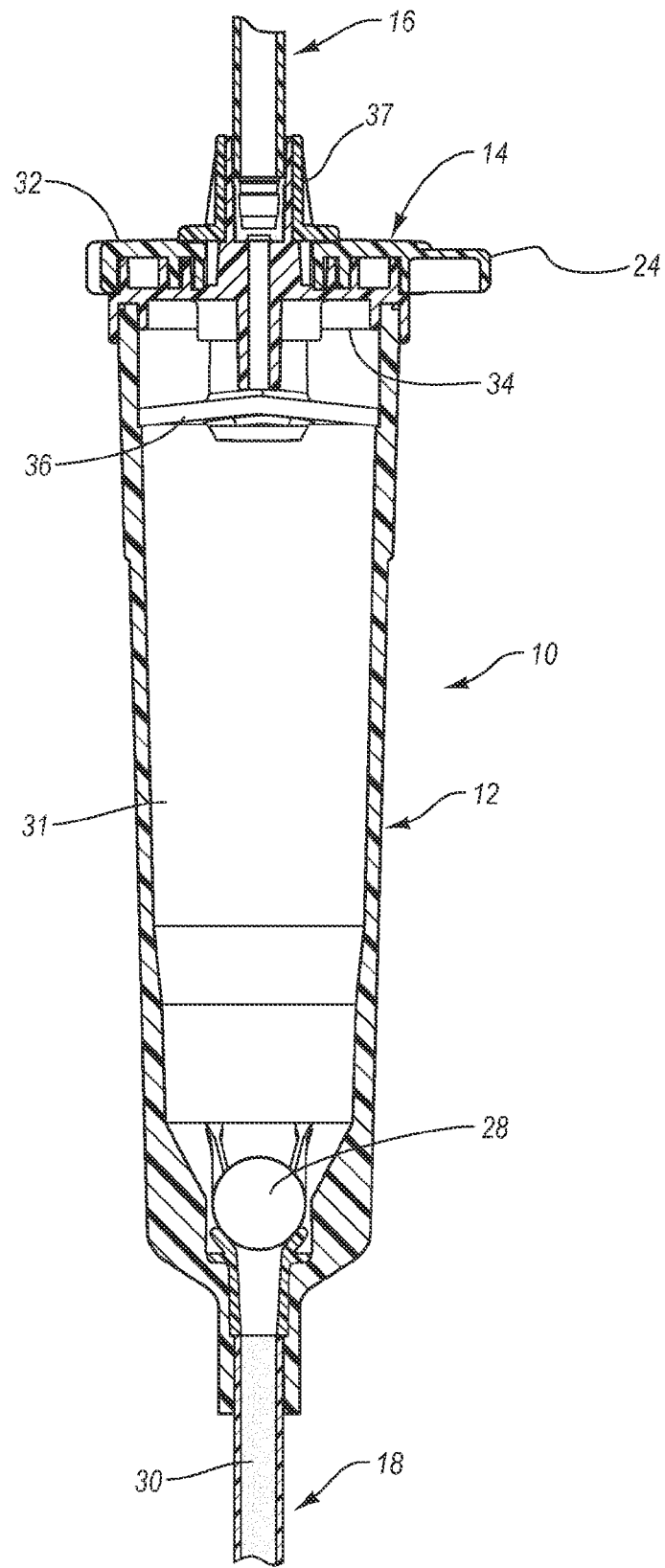
FIG. 2A is a front cut-away view of the contrast media delivery system of FIG. 1 illustrating the components of the flow regulator assembly according to one exemplary aspect of the present invention.

FIG. 2A is a partial cut-away view of the contrast media delivery system 10 depicted in FIG. 1. In the illustrated embodiment, a float 28 and chamber 31 are shown. Chamber 31 comprises the interior cavity of burette 12 and is configured to hold a volume of contrast media. Chamber 31 is shown substantially emptied of contrast media. Float 28 is positioned over the outlet of the burette 12. When float 28 is positioned over the outlet of burette 12, float 28 effectively occludes the lumen of outlet 18 and prevents the passage of air from chamber 31 to outlet 18. Additionally, the position of float 28 on the outlet of burette 12 maintains the volume of contrast media 30 in outlet 18 in an intact column.

In the illustrated embodiment, the components of flow regulator assembly 14 are depicted. Flow regulator assembly 14 comprises a rotatable cap 32, a seal housing 34, a diffuser 36, and a securement nut 37. In the illustrated embodiment, flow regulator assembly 14 is depicted in a normally closed position. When flow regulator assembly 14 is in the normally closed position, the flow of contrast media from inlet 16 to burette 12 is prevented.

Rotatable cap 32 comprises a mechanism which can be manipulated by the user to permit the flow of contrast media from inlet 16 into burette 12. Rotatable cap 32 comprises a substantially round disk which a user can grasp and rotate to open the seal utilized in connection with flow regulator assembly 14. Seal housing 34 is positioned between rotatable cap 32 and burette 12. Seal housing 34 provides a mechanism for securing the seal utilized to control the flow of contrast media from inlet 16 to burette 12. Seal housing 32 is rigidly secured to burette 12 and provides a secure base for mounting flow regulator assembly 14 to burette 12.

Diffuser 36 is secured to flow regulator assembly 14. Diffuser 36 provides a contact surface for controlling the flow of contrast media as the contrast media passes into burette 12. Diffuser 36 minimizes the formation of micro-bubbles or turbulence that can be formed as contrast media flows into burette 12. As contrast media passes from inlet 16 to burette 12, the contrast media flows along the diffusion surface of diffuser 36. The diffusion surface of diffuser 36 is configured to ensure that contrast media is relayed to the wall of burette 12. By relaying the contrast media to the walls of burette 12, diffuser 36 permits the contrast media to gradually enter the volume of contrast media in burette 12 from the walls of drip chamber 31 rather than falling freely from inlet 16 onto the surface of the volume of contrast media. In this manner, the formation of turbulence or micro-bubbles in the volume of contrast media that can result from falling droplets of contrast media is minimized.

Securement nut 37 is coupled to seal housing 34. Securement nut 37 maintains the position of rotatable cap 32 relative to the other components of flow regulator assembly 14. Securement nut 37 also allows rotatable cap 32 to perform the rotational movement desired during opening and closing of the seal associated with flow regulator assembly.

Figure 2B:
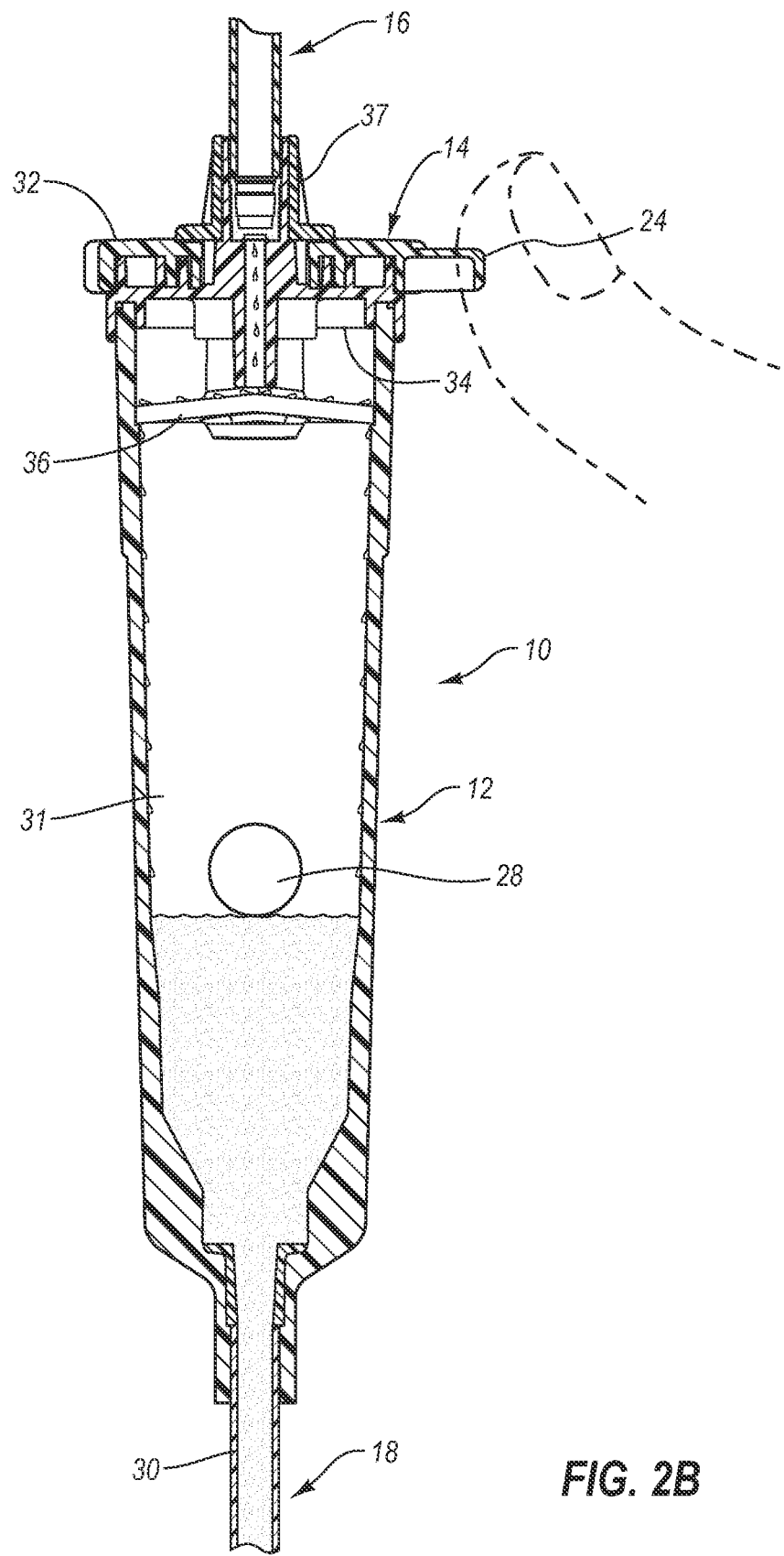
FIG. 2B is a front cut-away view of the contrast media delivery system of FIG. 1 illustrating actuation of the flow regulator assembly by a user according to one exemplary aspect of the present invention.

FIG. 2B is a partial cut-away view of contrast media delivery system 10 according to one exemplary embodiment of the present invention. In the illustrated embodiment, a user is depicted grasping rotatable cap 32 and/or first handle 24 of flow regulator assembly 14 and rotating rotatable cap 32. As a user rotates rotatable cap 32, a seal utilized in connection with flow regulator assembly 14 is opened permitting the passage of contrast media from inlet 16 to burette 12. In the illustrated embodiment, as the user rotates rotatable cap 32, the volume of contrast media flows from inlet 16 through seal housing 34 and onto a diffusion surface of diffuser 36. The diffusion surface of diffuser 36 channels the flow of contrast media to the interior wall of chamber 31. By channeling the flow of contrast media to the interior wall of chamber 31, the contrast media can gradually enter the volume of contrast media 30 within burette 12 without causing turbulence or other disturbance within the volume of contrast media 30.

In the illustrated embodiment, there is a sufficient volume of contrast media within burette 12 that air positioned above the volume of contrast media 30 will not inadvertently pass from burette 12 to outlet 18. As a result, float 28 is no longer needed to seal outlet 18 of burette 12. When float 28 is no longer needed to seal outlet 18 of burette 12, float 28 is designed to move from its sealing position (as shown in FIG. 2A) on the outlet of burette 12 to allow the passage of contrast media from burette 12 to outlet 18. The buoyant forces exerted on float 28 help to overcome any downward forces exerted on float 28 by the negative pressure in outlet 18. As a result, float 28 can separate from the outlet of burette 12. In this manner, float 28 moves to the surface of the volume of contrast media 30 until the contrast media in burette 12 empties and float 28 is again utilized to prevent the passage of air into outlet 18. Float 28 can also be utilized as a contact surface for droplets that stray from the wall of drip chamber 31. In other words, droplets may contact the upper surface of float 28 rather than dropping directly into the volume of contrast media.

In the illustrated embodiment, flow regulator assembly 14 is configured to be in a normally closed position. When the user grasps and rotates first handle 24 and/or rotatable cap 32, flow regulator assembly 14 is opened allowing the passage of contrast media from inlet 16 to burette 12. However, when a user releases the grasp on rotatable cap 34, rotatable cap 32 automatically returns to the normally closed position and the flow of contrast media from inlet 16 to burette 12 is stopped. As discussed with reference to FIG. 1, first handle 24 and second handle 26 (see FIG. 1) allow a user to simply and efficiently determine the desired amount of rotation of rotatable cap 32 to open the seal and allow the flow of contrast media. When rotatable cap 32 has been rotated the desired amount of rotation, first handle 24 and second handle 26 (see FIG. 1) will be aligned.

Figure 2C:
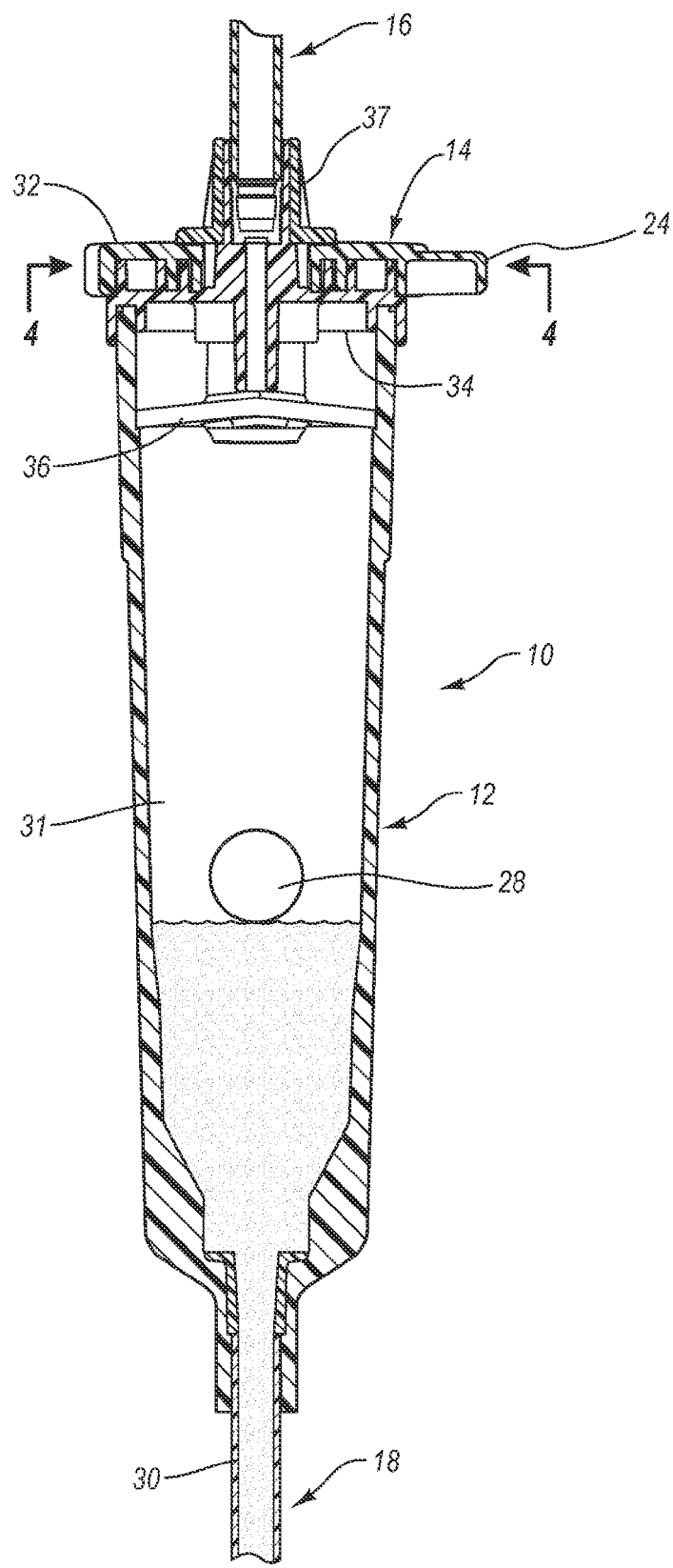
FIG. 2C is a front cut-away view of the contrast media delivery system of FIG. 1 illustrating the manner in which the flow regulator assembly automatically returns to a closed position when the user releases his/her grasp on the flow regulator assembly according to one exemplary aspect of the present invention.

FIG. 2C illustrates contrast media delivery system 10 in which the user has released the grasp on rotatable cap 32. When the user releases the grasp on rotatable cap 32 the seal associated with the flow regulator assembly 14 automatically closes and the passage of fluid from inlet 16 to burette 12 is stopped. As discussed with reference to FIG. 1, first handle 24 and second handle 26 (see FIG. 1) allow a user to simply and efficiently determine the desired amount of rotation of rotatable cap 32 to open the seal and allow the flow of contrast media. When a user desires to allow the closure of rotatable cap 32, the user simply releases first handle 24 such that it returns to a position out of alignment with second handle 26 (see FIG. 1). When first handle 24 is out of alignment with second handle 26 (see FIG. 1), free flowing of contrast media to burette 12 is stopped.

Because there is a volume of contrast media 30 in burette 12, when the practitioner utilizes a syringe to deliver contrast media to the patient, passage of fluid from chamber 31 into outlet 18 is permitted. Additionally, because the seal provided in connection with flow regulator assembly 14 is closed, delivery of contrast media from chamber 31 to the patient will begin to create a vacuum within chamber 31. As a result, contrast media will automatically be drawn from the source of contrast media into chamber 31 such that the level of contrast media within burette 14 remains relatively unchanged. This allows a user to release rotatable cap 31 to prevent the passage of additional contrast media into burette 12 without stopping the flow of contrast media to the patient. The ability to allow contrast media to flow from burette 12 to the patient, even when the valve associated with flow regulator assembly 14 is closed, may be desirable in some clinical settings. For example, a practitioner may desire to continue the flow of contrast media to a patient, even where the practitioner's attention is directed to other aspects of the procedure being performed. In some circumstance, the practitioner may close the stop cock (not shown) positioned between inlet 16 and the source of contrast media to empty any remaining contrast media positioned in chamber 31. The ability to allow the passage of contrast media to patient while discontinuing the flow of contrast media from the contrast media source to the burette may be desirable at the end of a procedure where the amount of contrast media in burette 12 is sufficient to complete the procedure.

When the volume of contrast media 30 in burette 12 again falls below a threshold level, float 28 will return to the outlet of burette 12 to prevent the passage of air into outlet 18 as depicted in FIG. 2A. In this manner, flow regulator assembly 14 can be utilized in connection with float 28 to closely monitor and regulate the usage of contrast media and the delivery of the contrast media to the patient while minimizing the potential that air bubbles may be introduced into outlet 18 of contrast media delivery system 10.

Figure 3:
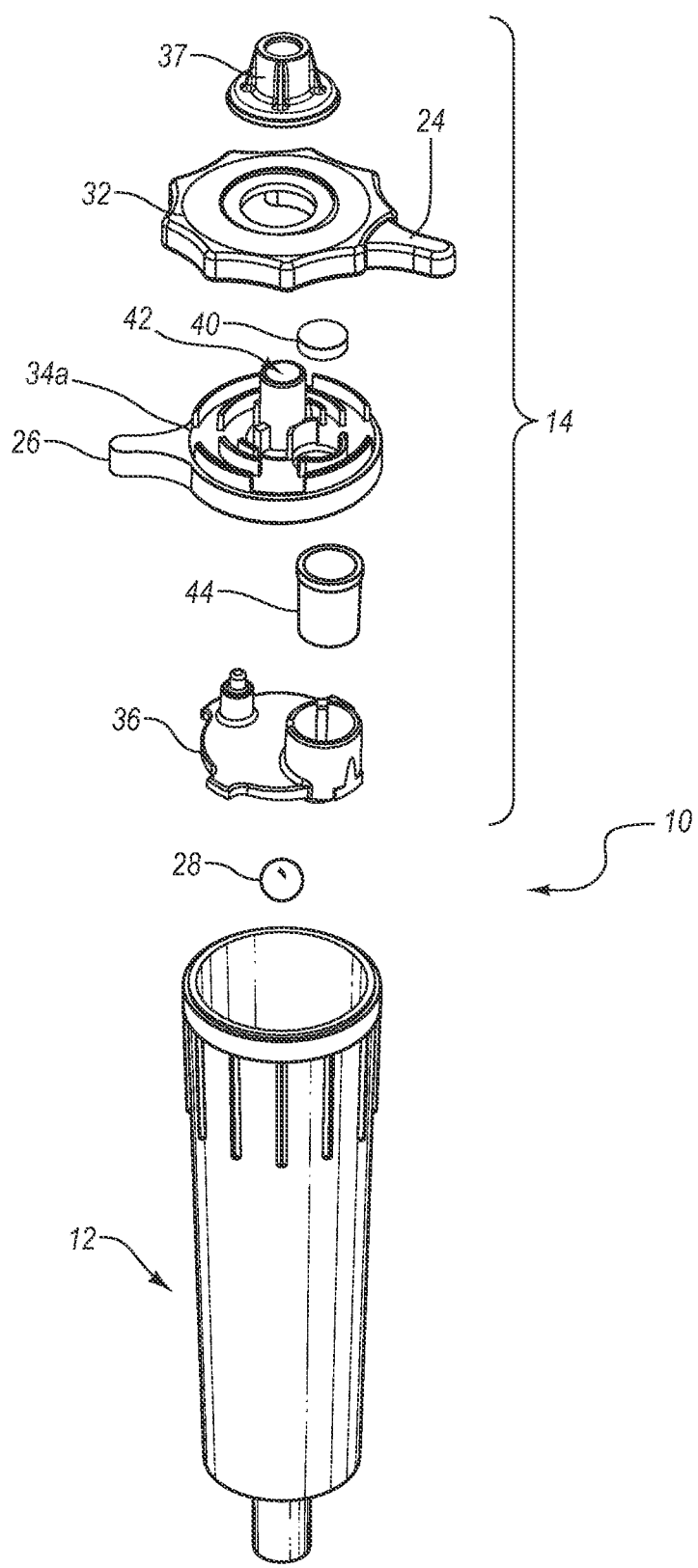
FIG. 3 is an exploded perspective view of the contrast media delivery system of FIG. 1 according to one exemplary aspect of the present invention.

FIG. 3 is an exploded perspective view of a contrast media delivery system 10 according to one embodiment of the present invention. In the illustrated embodiment, the components of flow regulator assembly 14 are illustrated. Flow regulator assembly 14 comprises a rotatable cap 32, a vent seal 40, a seal housing 34, a filter 44, a diffuser 36, and a securement nut 37. Vent seal 40 is positioned in seal housing 34. Vent seal 40 is configured to selectively allow the passage of air from burette 12 to the exterior of contrast media delivery system 10. By selectively allowing the passage of air from the interior of contrast media delivery system 10, the flow of contrast media through the contrast media delivery lumen 42 of seal housing 34 is also controlled. In other words, for contrast media to pass through flow regulator assembly 14 and into burette 12, air must be allowed to escape from burette 12. By utilizing vent seal 40 to control the passage of air, the user indirectly controls the passage of contrast media into burette 12. Vent seal 40 is one example of a sealing mechanism.

Rotatable cap 32 is positioned around the post of seal housing 34 such that rotatable cap 32 is positioned on the upper surface of seal housing 34. The juxtaposition of rotatable cap 32 and seal housing 34 secures vent seal 40 in its proper position within flow regulator assembly 14. Securement nut 37 is coupled to the post of seal housing 34 to effectively secure rotatable cap 32 relative to the other components of flow regulator assembly. Additionally, the engagement of securement nut 37 to the post of seal housing 34 permits rotatable cap 32 to rotate relative to seal housing 34. The rotational movement of rotatable cap 32 deforms vent seal 40 in a manner that allows air to escape from burette 12.

In the illustrated embodiment, rotatable cap 32 includes first handle 24 and seal housing 34 includes second handle 26. When the flow regulator assembly 14 is in a released position, first handle 24 and second handle 26 are not in alignment. When flow regulator assembly 14 is in a released position, the free flow of contrast media from inlet 16 to burette 12 is not permitted. To begin the flow of contrast media, as previously discussed, the user manipulates first handle 24 in the direction of second handle 26. This rotates seal housing 34 to a desire position causing a desired deformation of vent seal 40. When vent seal 40 is deformed, the free flow of contrast media is allowed. By utilizing a handle 24 in connection with handle 26, the user can simply and reliably identify when the components of rotatable cap 32 and seal housing 34 have been moved to the desired position to allow for the flow of contrast media.

A filter 44 is positioned between seal housing 34 and diffuser 36. Filter 44 ensures that any moisture or contrast media positioned between diffuser 36 and seal housing 34 does not obstruct the passage of air moving past vent seal 40. Filter 44 acts as a barrier to prevent impurities or agents, such as bacteria, from entering the fluid path or within burette 12. In other words, Filter 44 ensures that bacteria from outside the burette does not enter the burette. Filter 44 also prevents or minimizes the inadvertent escape of contrast media from burette 12.

Diffuser 36 is positioned such that contrast media emerging from contrast media delivery lumen 42 passes to the diffusion surface of diffuser 36. The tapered configuration of the diffusion surface of diffuser 36 directs the flow of contrast media from the central position of contrast media delivery lumen 42 to the inner walls of burette 12. As a result, the contrast media flows smoothly and without interruption along the walls of burette 12. The flow of contrast media along the walls of burette 12 minimizes any droplets or splashing on the surface of the volume of contrast media within burette 12. In this manner, diffuser 36 minimizes turbulence or the formation of microbubbles in the volume of contrast media.

As will be appreciated by those skilled in the art, a variety of types and configurations of flow regulator assemblies can be utilized without departing from the scope and spirit of the present invention. For example, according to one embodiment of the present invention, the seal associated with the flow regulator assembly directly controls the flow of contrast media rather than indirectly controlling the flow of contrast media by controlling the passage of air from the burette. According to another embodiment of the present invention, a first seal or valve is utilized to directly control the flow of contrast media and a second seal or valve is utilized to indirectly control the flow of contrast media. According to another embodiment of the present invention, a moveable member is operably linked to the other components of the flow regulator assembly allowing the moveable member to be manipulated by the user other than by using rotational force and to control the passage of fluid through contrast media delivery system. For example, according to one embodiment of the present invention, a lever is provided which can be manipulated by the user to control the flow of contrast media. According to another embodiment of the present invention, the flow regulator assembly has a plurality of positions that can be utilized rather than just a normally closed and a normally open position. According to yet another embodiment of the present invention, the flow regulator assembly is utilized without a diffuser.

Figure 4A:
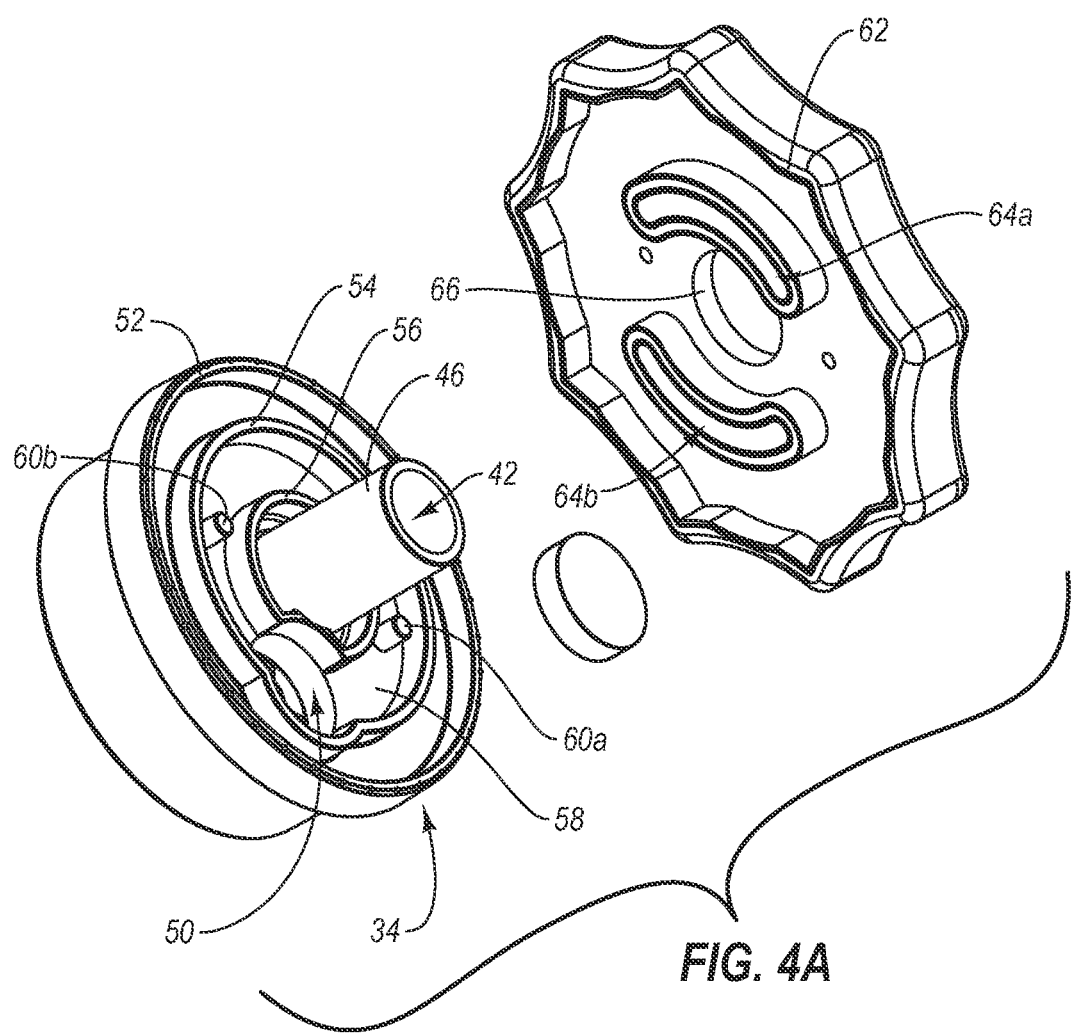
FIG. 4A is a component view of the flow regulator assembly of FIG. 1 illustrating a seal housing, a seal, and a movable member according to one exemplary aspect of the present invention.

FIG. 4A illustrates rotatable cap 32, seal housing 34, and vent seal 40 according to one embodiment of the present invention. In the illustrated embodiment, vent seal 40 is configured to be positioned between rotatable cap 32 and seal housing 34. Vent seal 40 is positioned within a vent seal seat 50 of seal housing 34. Vent seal 40 provides an effective mechanism for occluding the passage of air from the under side of seal housing 34 to the exterior of the contrast media delivery system through vent seal seat 50.

Seal housing 34 comprises a contrast media delivery lumen 42, a vent seal seat 50, an outer guide ring 52, an intermediate guide ring 54, an inner guide ring 56, a rotation track 58, and guides 60a,b. Contrast media delivery lumen 42 allows the passage of contrast media from an inlet 16 (see FIG. 2A) to the interior of burette 12 (see FIG. 2A). Contrast media delivery lumen 42 is defined by an inner cylinder 46. Inner cylinder 46 not only defines contrast media delivery lumen 42, but also provides a securement post to which rotatable cap 32 is mounted. Outer guide ring 52, intermediate guide ring 54, and inner guide ring 56 facilitate the rotation of rotatable cap 32 relative to seal housing 34. The description of outer guide ring 52, intermediate guide ring 54, and inner guide ring 56 and their operation relative to rotatable cap 32 will be described in greater detail hereinafter.

In the illustrated embodiment, rotatable cap 32 includes an outer rim 62, channel guides 64a,b, and a central aperture 66.

Outer rim 62 is configured to be cooperatively positioned around outer guide ring 52 in a manner that allows for rotational movement of rotatable cap relative to seal housing 34. The cooperative engagement of outer rim 62 and outer guide ring 52 maintains the defined rotational movement of rotatable cap 32 relative to seal housing 34. The scalloped configuration of outer rim 62 provides a tactile surface allowing a user to simply and efficiently grasp and manipulate rotatable cap 32. Rotation of rotatable cap 32 permits the passage of contrast media through seal housing 34 by opening an air vent to atmosphere.

Channel guides 64a,b are positioned on the under side of rotatable cap 32. Channel guides 64a,b are configured to be positioned within rotation track 58. In other words, channel guides 64a, b are positioned between intermediate guide ring 54 and inner guide ring 56. An inner channel is defined by the outer perimeter of channel guides 64a,b. The inner channel is configured to be positioned over guides 60a,b. The curved configuration of channel guides 64a,b maintains the position of rotatable cap 32 and channel guides 64a,b as the user rotates rotatable cap 32 relative to seal housing 34.

Central aperture 66 is positioned at the center of rotatable cap 32. Central aperture 64 allows rotatable cap 32 to be positioned over inner cylinder 46 of seal housing 34. The circumferential contact between the outer contact surface of inner cylinder 46 and the wall of central aperture 66 helps to facilitate rotational movement of rotatable cap 32 relative to seal housing 34.

Figure 4B:
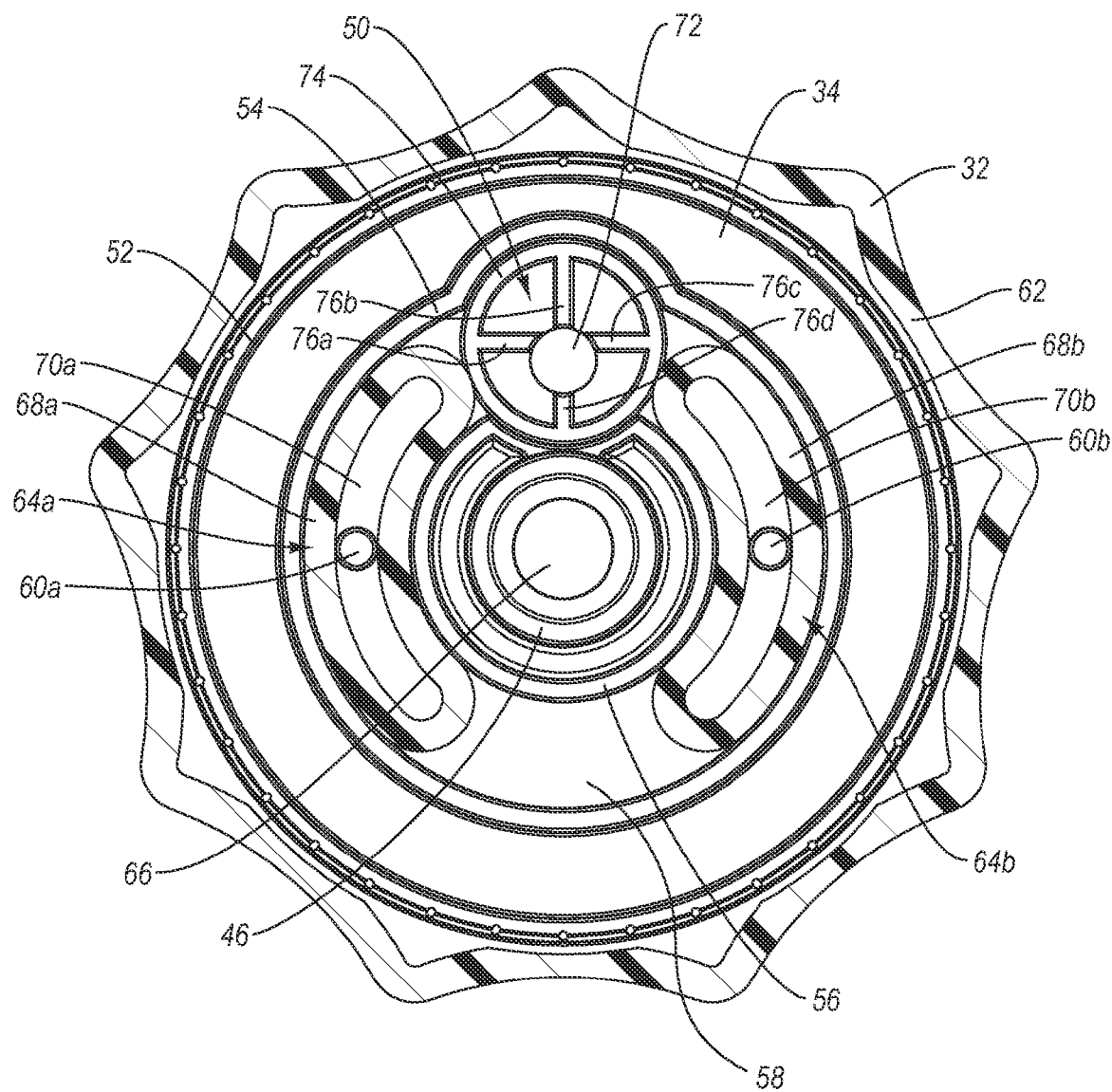
FIG. 4B is a partial cross-sectional view of the flow regulator assembly of FIG. 1 illustrating operation of the movable member relative to the seal housing according to one exemplary aspect of the present invention.

FIG. 4B is a partial cross-sectional view of flow regulator assembly 14 (see FIG. 2C) taken along lines 4-4 of FIG. 2C according to one embodiment of the present invention. In the illustrated embodiment, the upper surface of seal housing 34 is shown while rotatable cap 32 is shown in cross section so as to more clearly illustrate the juxtaposition of the components of rotatable cap 32 relative to seal housing 34. Outer guide ring 52 of seal housing 34 is positioned to be in contact with the inner surface of outer rim 62. The juxtaposition of outer rim 62 relative to outer guide ring 52 allows for the rotational movement of rotatable cap 34 while also maintaining the position of rotatable cap 32 relative to seal housing 34.

The position of channel guides 64a,b relative to rotation track 58 of seal housing 34 and guides 60a,b is also illustrated. In the illustrated embodiment, channel guides 64a,b comprise walls 60a,b and slots 70a,b. In other words, channel guide 64a comprises a wall 68a and a slot 70a. Channel guide 64b comprises a wall 68b and a slot 70b. Wall 68a of channel guide 64a is positioned within rotation track 58 such that wall 68a contacts intermediate guide ring 54 on one side of channel guide 64a and contacts inner guide ring 56 on the other side of channel guide 64a. Guide 60a of seal housing 34 is positioned within slot 70a of channel guide 64a such that guide 60a contacts both sides of wall 68a. Similarly, wall 68b of channel guide 64b is positioned within rotation track 58 such that wall 68b contacts intermediate guide ring 54 on one side of channel guide 64b and contacts inner guide ring 56 on the other side of channel guide 64b. Guide 60b of seal housing 34 is positioned within slot 70b of channel guide 64b such that guide 60b contacts both sides of wall 68b. By providing a plurality of channel guides for use with rotation track 58, smooth and reliable rotation of rotatable cap 32 relative to seal housing 34 is maintained. Additionally, the juxtaposition of channel guides 64a and 64b relative to intermediate guide ring 54, inner guide ring 56, and guides 60a,b provides a plurality of contact points between rotatable cap 32 and seal housing 34. The plurality of contact points between rotatable cap 32 and seal housing 34 facilitates smooth and reliable rotation of rotatable cap 32 relative to seal housing 34.

As will be appreciated by those skilled in the art, a variety of channels, guides and other mechanisms permitting the smooth and reliable rotation of rotatable cap 32 relative to seal housing can be utilized without departing from the scope and spirit of the present invention. For example, according to one embodiment of the present invention, the guide rings are replaced by segmented guide walls as depicted in of FIG. 3 with reference to seal housing 34a. According to another embodiment of the present invention, locking guides and slide mechanisms are provided. According to another embodiment of the present invention, one or more additional members are provided in addition to the rotatable cap and seal housing to facilitate rotational movement.

In the illustrated embodiment, vent seal seat 50 is illustrated. Vent seal seat 50 includes a vent aperture 72, a circumferential channel 74, and intersecting channels 76a,b,c,d. In the illustrated embodiment, vent aperture 72 provides a passageway between the under side of seal housing 34 and the area between seal housing 34 and rotatable cap 32. According to one embodiment of the present invention the area between rotatable cap 32 and seal housing 34 is not sealed from the ambient environment. As a result, the air that passes through vent aperture 72 from burette 12 is vented directly to the external ambient environment.

Circumferential channel 74 is positioned in communication with an aperture 72 by use of intersecting channels 76a, b,c,d. When vent seal 40 (see FIG. 4A) is positioned within vent seal seat 50, any deformation of vent seal 40 (see FIG. 4A) will allow the passage of air through vent aperture 72, circumferential channel 74 and/or one or more of intersecting channels 76a,b,c,d. In this manner, any separation between the seal and one or more of circumferential channel 74 and/or intersecting channels 76a,b,c,d will allow air to pass to the external environment through vent aperture 72.

As will be appreciated by those skilled in the art, a variety of types and configurations of vents can be utilized without departing from the scope and spirit of the present invention. For example, according to one embodiment of the present invention a simple cross shaped vent is provided with the entire length of each arm of the cross providing venting communication through the seal housing. According to another embodiment of the present invention, a simple circular or non-circular shaped vent is provided. According to another embodiment of the present invention, the vent is integral with the seal or valve utilized to control the passage of air through the vent.

Figure 4C:
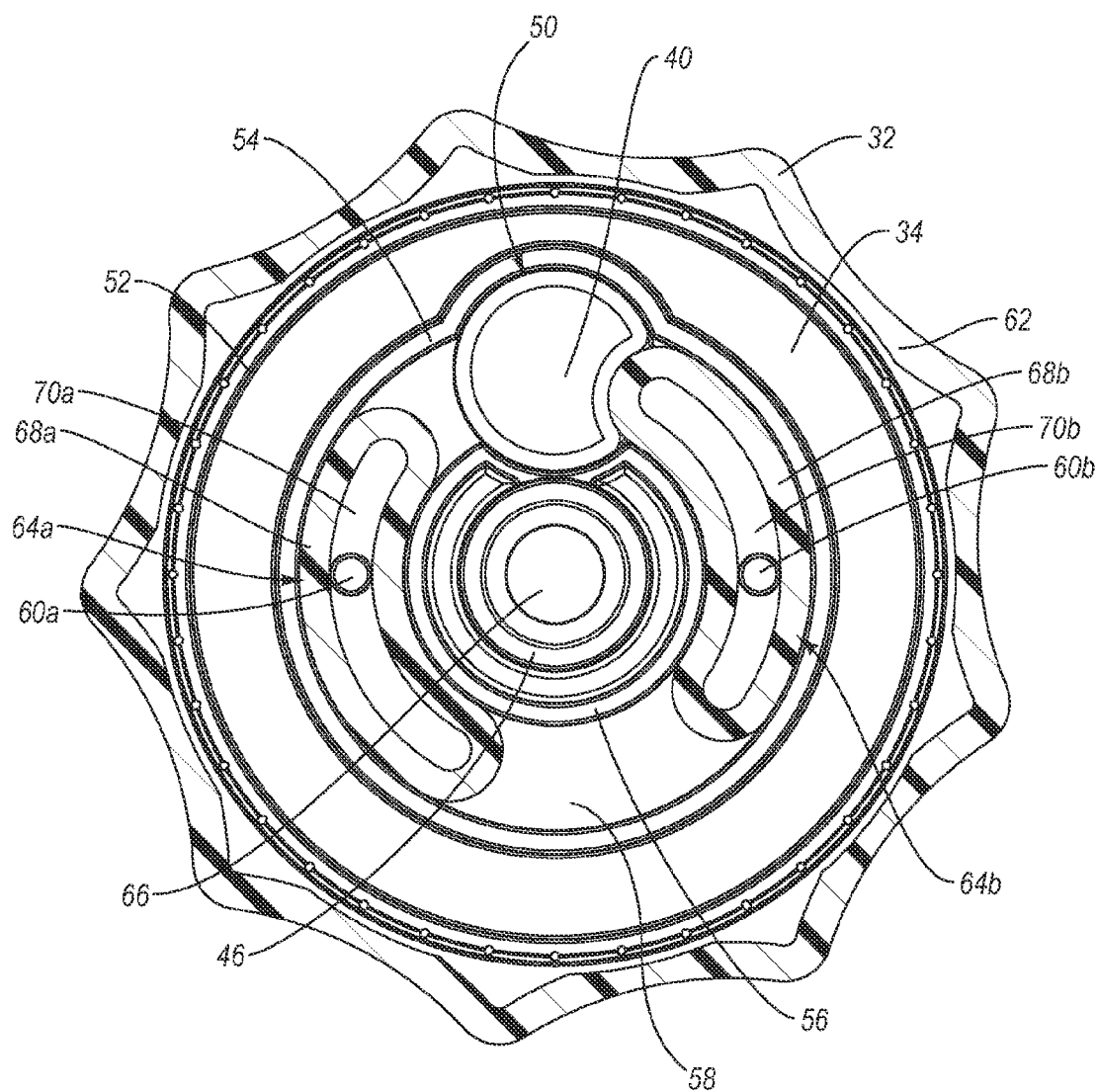
FIG. 4C is a partial cross-sectional view of the flow regulator assembly of FIG. 4A illustrating the manner in which the movable member can open the seal according to one exemplary aspect of the present invention.

FIG. 4C illustrates the manner in which rotation of rotatable cap 32 opens vent seal 40 and allows the passage of air to the external environment from within burette 12 (see FIG. 2A). In the illustrated embodiment, vent seal 40 is positioned within vent seal seat 50. Vent seal 40 comprises a substantially disk-shaped member which can be comprised of a variety of materials including silicone, rubber, thermoplastic elastomers or other appropriate sealing materials. When a user manipulates rotatable cap 32, one of channel guides 64a,b will come in contact with vent seal 40. In the illustrated embodiment, channel guide 64b is shown contacting vent seal 40.

When sufficient rotational force is exerted on a rotatable cap 32, the interaction between one of channel guides 64a,b and vent seal 40 deforms the shape of vent seal 40. Deformation of vent seal 40 separates one or more portions of vent seal 40 from one or more of vent aperture 72, circumferential channel 74, and/or intersecting channels 76a,b,c,d (see FIG. 4B). As a result, the passage of air is permitted through vent aperture 72 (see FIG. 4B), and into the external environment. Thus, such components may cooperatively comprise a boundary forming a fluid barrier along at least a portion of a perimeter of the seal. When a user releases rotatable cap 32 such that rotational forces are no longer exerted on the rotatable cap 32, the resilient properties of vent seal 40 exert a force on the one of channel guides 64a,b which is deforming the vent seal 40. By exerting a force on the one of channel guides 64a,b, vent seal 40 returns to its original configuration while also causing the rotation of rotatable cap 32 to the position depicted in FIG. 4B.

As will be appreciated by those skilled in the art, the configuration of rotatable cap 32 and seal housing 34 allow a user to rotate rotatable cap 32 in either a clockwise or counterclockwise direction to deform vent seal 40. When vent seal 40 is deformed, the passage of air is permitted from the interior of burette 12, through vent aperture 72 (see FIG. 4B) and to the external environment. The venting of air from the interior of burette 12 allows the passage of contrast media from the contrast media source, through contrast media delivery lumen 42 and into the burette 12 (see FIG. 2B). It also allows air to enter the burette from the external environment (through the filter 44 of FIG. 3) thus eliminating the vacuum that is created when the fluid in the burette is depleted.

By controlling the flow of contrast media indirectly, the contrast media does not contact the seal or valve utilized with the flow regulator assembly. In this manner, the material properties of the contrast media do not affect the operation or performance of the seal or valve that is utilized to control the flow of contrast media. The use of a vent seal provides a simple, reliable, and effective mechanism for controlling the passage of contrast media from a contrast media delivery source to the interior of the burette and then on to the patient. Additionally, by allowing a user to manipulate rotatable cap 32 in either a clockwise or counterclockwise direction to facilitate the flow of contrast media, flow regulator assembly 14 provides a straightforward operation which is intuitive for doctors and other practitioners utilizing contrast media delivery system 12.

As will be appreciated by those skilled in the art, a variety of types and configurations of seals or valves can be utilized without departing from the scope and spirit of the present invention. According to one embodiment, a valve is utilized which directly interacts with the contrast media to permit or stop the passage of fluid into the burette. In another embodiment, the operation of contrast media delivery to the burette is separated from the operation of the valve. In another embodiment, a bicuspid or tricuspid valve is utilized. In another embodiment, a Tuohy Borst valve or valve/introducer combination is utilized to open and close a valve. In another embodiment, a non-disk-shaped valve is provided.

Figure 5:
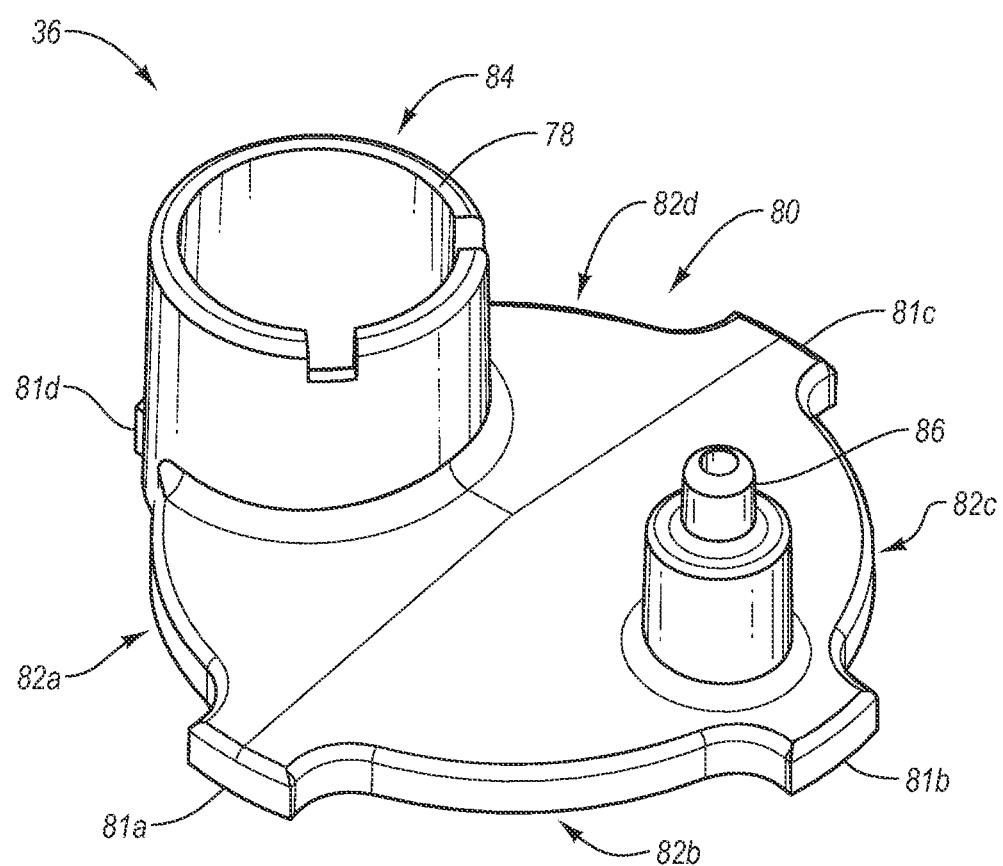
FIG. 5 is a perspective view of the diffuser of the flow regulator assembly according to one exemplary aspect of the present invention.

FIG. 5 is a perspective view of a diffuser 36 for use with the contrast media delivery system 10 of FIG. 1, according to one aspect of the present invention. In the illustrated embodiment, diffuser 36 includes an anti-splash barrier 78, a diffusion surface 80, contact flanges 81a,b,c,d, flow edges 82a,b,c,d, a filter receptacle 84, and snap fitting 86. Contrast media delivery lumen of the seal housing 34 is positioned above the diffusion surface 80. The anti-splash barrier 78 is positioned so as to isolate diffusion surface 80 from the filter receptacle 84 as contrast media passes from seal housing 34 to diffusion surface 80.

As contrast media passes from the seal housing 34, it contacts diffusion surface 80. Diffusion surface 80 is tapered to facilitate the flow of contrast media along the face of diffusion surface 80 to the edge of diffuser 36. In the illustrated embodiment, diffusion surface 80 is tapered radially to facilitate the distribution of contrast media along the outer periphery of diffuser 36. Diffuser 36 is secured relative to burette 12 utilizing contact flanges 81a,b,c,d.

As contrast media flows along diffusion surface 80, it passes to flow edges 82a,b,c,d. Flow edges 82 are positioned between contact flanges 81a,b,c,d. In other words, flow edge 82a is positioned between contact flanges 81a and 81d. Flow edge 82b is positioned between contact flanges 81a and 81b. Flow edge 82c is positioned between contact flanges 81b and 81c. Flow edge 82d is positioned between contact flanges 81c and 81d. Flow edges 82a,b,c,d have a defined displacement relative to the inner wall of burette 12 (see FIG. 2B). The defined displacement between flow edges 82a,b,c,d comprise an opening which facilitates the passage of fluid from diffusion surface 80 to burette 12 (see FIG. 2B.) Flow edges 82a,b,c,d are configured to control the passage of contrast media from diffusion surface 80 to an internal wall of burette 12 (see FIG. 2B). The tapered configuration of diffusion surface 80 and flow edges 82a,b,c,d, help to evenly allocated contrast media along the circumference of diffuser 36. In this manner, pooling or collection of contrast media at a single point along the circumference of diffuser 36 that could interrupt the flow of contrast media into burette 12 (see FIG. 2B) is minimized.

Filter receptacle 84 accommodates filter 44 (see FIG. 3) such that filter 44 (see FIG. 3) is positioned between seal housing 34 and diffuser 36 (see FIG. 3). Filter 44 (see FIG. 3) ensures that bacteria from outside the burette does not enter the burette. Snap fitting 86 allows the coupling of diffuser 36 to seal housing 34. In this manner, the position of diffuser 36 relative to the other components of contrast media delivery system 10 is secured.

As will be appreciated by those skilled in the art, a variety of types and configurations of diffusers can be utilized without departing from the scope and spirit of the present invention. For example, according to one embodiment of the present invention, the diffuser includes first and second components which diffuse the contrast media along the outer circumference of the burette. According to another embodiment of the present invention, the diffuser minimizes turbulence by directing the flow of contrast media directly into the volume of contrast media within the burette. According to another embodiment of the present invention, the entire circumference of the diffuser is configured to channel contrast media rather than just a portion of the surface of the diffuser.

Figure 6A:
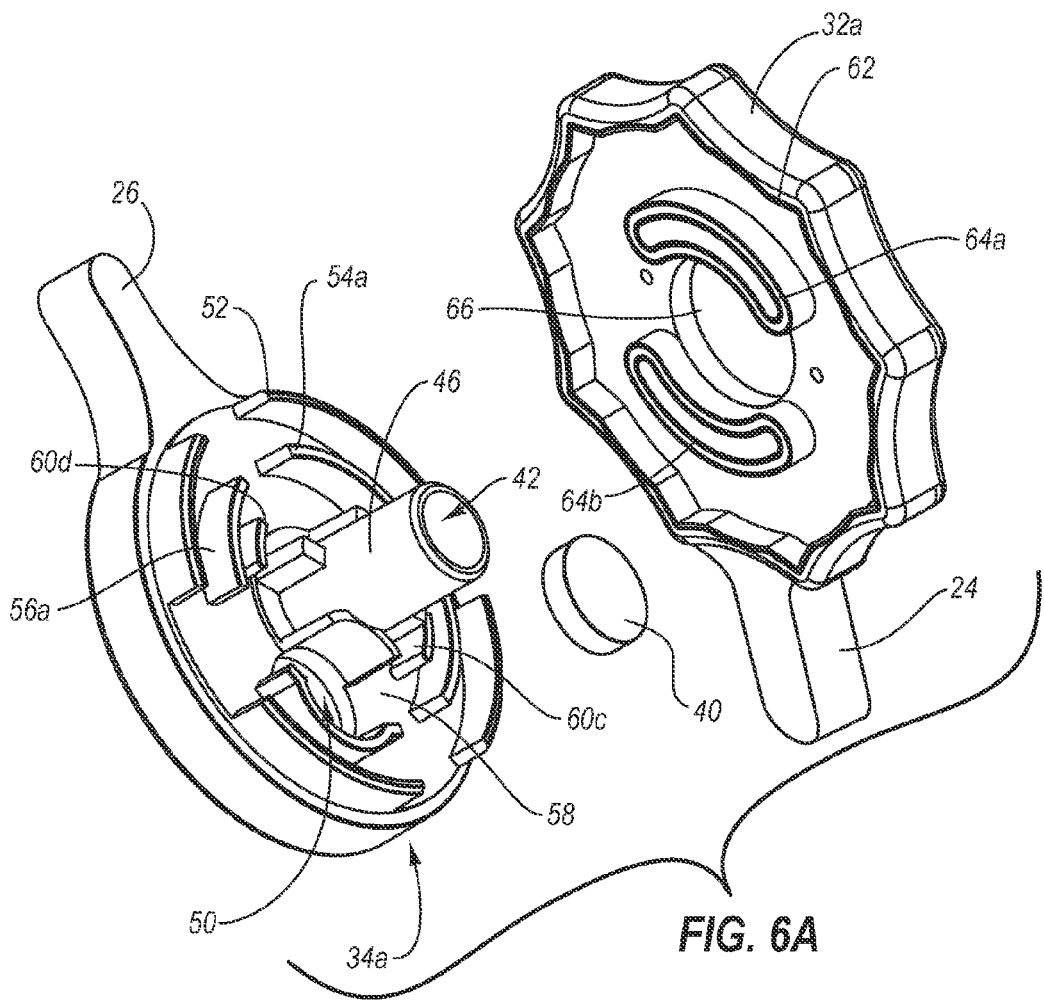
FIG. 6A is a component view of an alternate flow regulator assembly according to one exemplary aspect of the present invention.
Figure 6B:
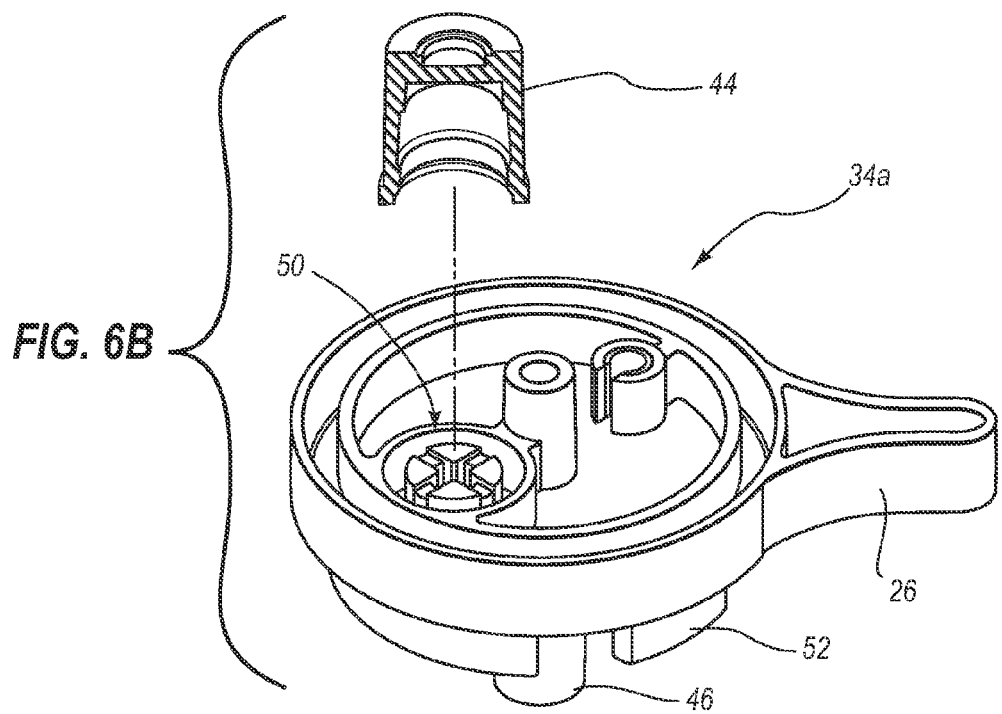
FIG. 6B is a perspective bottom view of a seal housing and filter of FIG. 6A according to one exemplary aspect of the present invention.

FIGS. 6A and 6B illustrate rotatable cap 32a, seal housing 34a, vent seal 40, and filter 44 according to one alternative aspect of the present invention. Rotatable cap 32a and seal housing 34a is similar to the rotatable cap 32 and seal housing of seal housing 34a. However, rotatable cap 32a and seal housing 34a also include a number of differences from the apparatus depicted in FIG. 4A in several respects.

In the illustrated embodiment, vent seal 40 is positioned within a vent seal seat 50 of seal housing 34a. Vent seal 40 provides an effective mechanism for occluding the passage of air from the under side of seal housing 34a to the exterior of the contrast media delivery system through vent seal seat 50. As depicted with reference to FIG. 6B, filter 44 is adapted to be positioned on the underside of vent seal seat 50. In the illustrated embodiment, filter 44 comprises a housing which accommodates a filter paper. Filter 44 minimizes the passage of fluid from the underside of rotatable seal housing 34a to vent seal seat 50 which could interfere with the proper operation of vent seal 40.

In the illustrated embodiment, rotatable cap 32a includes first handle 24 and seal housing 34a includes second handle 26. When first handle 24 and second handle 26 are not in alignment (see FIG. 1), vent seal 40 remains in a sealed configuration and the flow of air through vent seal seat 50 is not permitted. When the flow of air through vent seal seat 50 is not permitted, the free passage of contrast media through contrast media delivery lumen 42 is stopped. As a result, contrast media will only flow to maintain the level of contrast media in burette 12 (see FIG. 2B).

To begin the flow of contrast media such as to increase the level of contrast media in burette 12 (see FIG. 2B), as previously discussed, the user manipulates first handle 24 in the direction of second handle 26. When first handle 24 is moved in the direction of second handle 26, vent seal 40 is deformed by one of channel guides 64a,b and the flow of air through vent seal seat 50 is permitted. When air flows through vent seal seat 50, the free passage of contrast media through contrast media delivery lumen 42 is permitted. By utilizing a handle 24 in connection with handle 26, the user can simply and reliably identify when the components of flow regulator assembly have been moved to the desired position to allow for the flow of contrast media.

In the illustrated embodiment, seal housing 34a comprises a contrast media delivery lumen 42, a vent seal seat 50, an outer guide ring 52a, an intermediate guide ring 54a, an inner guide ring 56a, a rotation track 58, and guides 60a,b. Contrast media delivery lumen 42 allows the passage of contrast media from an inlet 16 (see FIG. 2A) to the interior of burette 12 (see FIG. 2A). Contrast media delivery lumen 42 is defined by an inner cylinder 46. Inner cylinder 46 not only defines contrast media delivery lumen 42, but also provides a securement post to which rotatable cap 32a is mounted.

Outer guide ring 52a, intermediate guide ring 54a, and inner guide ring 56a facilitate the rotation of rotatable cap 32a relative to seal housing 34a. Outer guide ring 52a, intermediate guide ring 54a, and inner guide ring 56a are similar in function to outer guide ring 52, intermediate guide ring 54, and inner guide ring 56 described with reference to FIG. 4A. However, unlike outer guide ring 52, intermediate guide ring 54, and inner guide ring 56 described with reference to FIG. 4A, outer guide ring 52a, intermediate guide ring 54a, and inner guide ring 56a have broken wall segments to facilitate the molding of seal housing 34a and frictionless rotation of rotatable cap 32a relative to seal housing 34a.

In the illustrated embodiment, rotatable cap 32a includes an outer rim 62, channel guides 64a,b, and a central aperture 66. Outer rim 62 is configured to be cooperatively positioned around outer guide ring 52a in a manner that allows for rotational movement of rotatable cap relative to seal housing 34a. The cooperative engagement of outer rim 62 and outer guide ring 52a maintains the defined rotational movement of rotatable cap 32a relative to seal housing 34a. The scalloped configuration of outer rim 62 provides a tactile surface allowing a user to simply and efficiently grasp and manipulate rotatable cap 32a. Rotation of rotatable cap 32a permits the passage of contrast media through seal housing 34a by opening an air vent to atmosphere.

Channel guides 64a,b are positioned on the under side of rotatable cap 32a. Channel guides 64a,b are configured to be positioned within rotation track 58. In other words, channel guides 64a, b are positioned between intermediate guide ring 54a and inner guide ring 56a. An inner channel is defined by the outer perimeter of channel guides 64a,b. The inner channel is configured to be positioned over guides 60a,b. Channel guides 60c,d have a longer linear configuration compared with guides 60a,b depicted in FIG. 4A. The configuration of guides 60c,d facilitates the reliable and smooth movement of channel guides 64a,b during rotation of rotatable cap 32a relative to seal housing 34a.

Figures 7A, 7B:
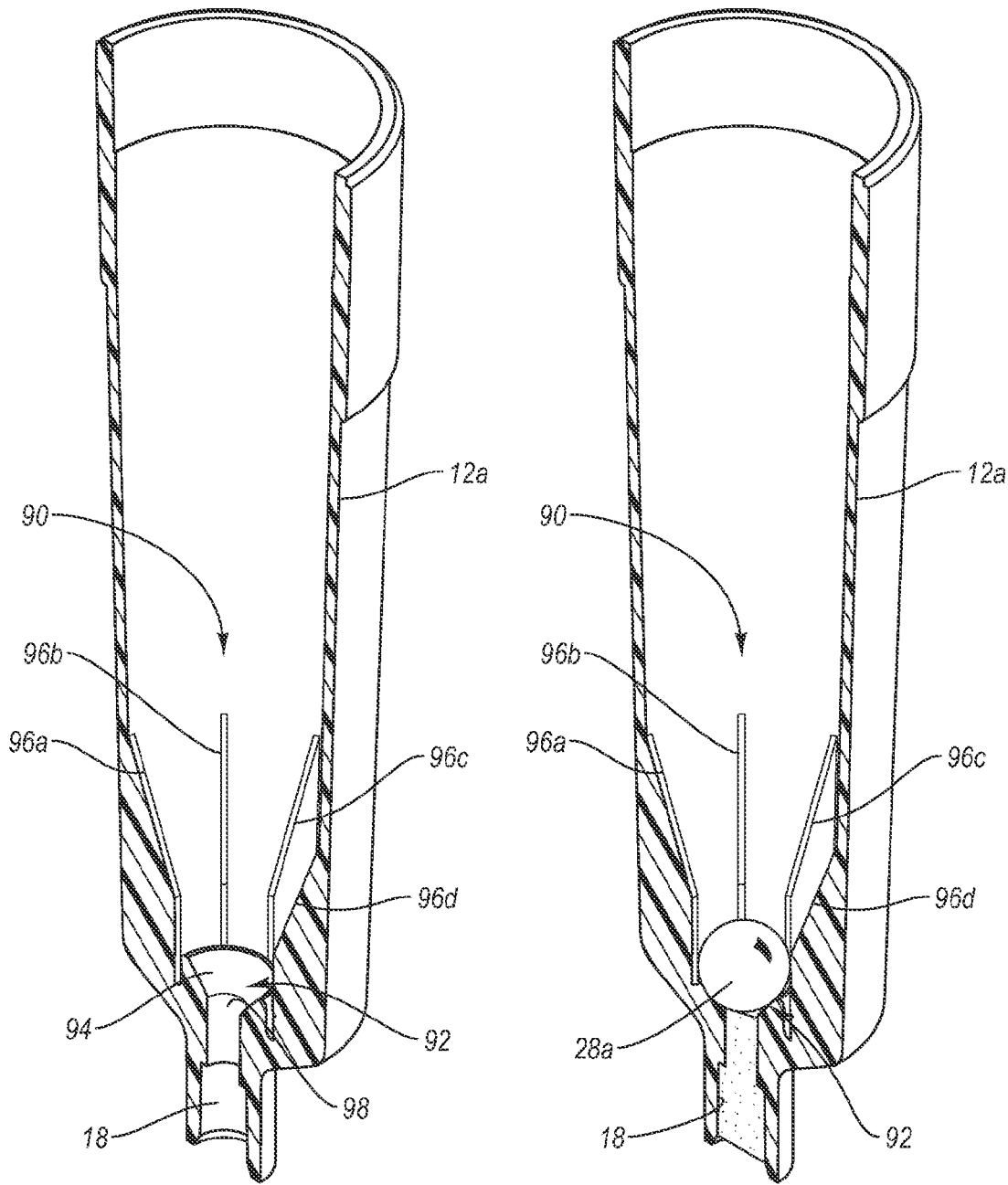
FIG. 7A is a front cut-away view illustrating a seat assembly of a contrast media delivery system according to one exemplary aspect of the present invention.
FIG. 7B is a front cut-away view illustrating operation of the float in connection with the seat assembly of FIG. 6A according to one exemplary aspect of the present invention.

FIG. 7A is a partial cut-away view of a burette 12a according to one embodiment of the present invention. In the illustrated embodiment, burette 12a includes a seating assembly 90 which provides desired sealing of the outlet of burette 12a while also allowing separation of a float from seat 98 when the burette is being filled with contrast media. In the illustrated embodiment, seating assembly 90 includes a seat 92, and projections 96a,b,c,d. Seat 92 is raised relative to the bottom of burette 12a. By being raised, a predetermined displacement between seat 92 and the bottom of the burette is provided. In this manner, a volume of fluid can be positioned between a float and the bottom of the burette when the float is resting on seat 92. Projections 96a,b,c,d are provided on the inner wall of drip chamber 31. Projections 96a,b,c,d are configured to guide a float to a desired position on seat 92 as the volume of contrast media within burette 12a empties. In this manner, a practitioner can direct his/her attention to other aspects of the procedure to be performed rather than needing to ensure that the float is being properly positioned on seat 92.

In the illustrated embodiment, seat 92 includes a contact surface 94 and a central aperture 98. Contact surface 94 is configured to accommodate a float utilized in connection with seat 92. The primarily circumferential configuration of contact surface 94, shown in the illustrated embodiment, is adapted to accommodate a spherical or rounded bottom float. Central aperture comprises an exit aperture for contrast media passing from burette 12a to outlet 18. When a float is positioned on contact surface 94, central aperture 98 is effectively sealed and the passage of additional contrast media or air into outlet 18 is prevented FIG. 7B illustrates a float 28a positioned on seat 92 according to one embodiment of the present invention. In the illustrated embodiment, the volume of contrast media within burette 12a is sufficiently reduced such that ball 28a is positioned on contact surface 94 (see FIG. 7A) of seat 92. Float 28a is configured to provide a complete seal over central aperture 98. In this manner, contrast media in outlet 18 is maintained in a fluid column and the introduction of air into outlet 18 is minimized. A volume of contrast media is also present between the bottom of the burette 12a and the top of seat 92. The volume of contrast media between the bottom of burette 12 and seat 28a provides a buoyant force when additional contrast media is introduced into burette 12a. The buoyant forces resulting from the rising volume of contrast media can overcome the suction exerting a downward pressure on float 28a. In this manner, float 28a can be separated from seat 92 when burette 12a is being refilled with contrast media. As a result, a user is not required to shake or agitate the burette 12a to separate seat 92 from float 28a. In other words, the configuration of seat 92 provides sufficient contact surface between contrast media in burette 12a and the underside of float 28a to separate float 28a from the vacuum effect created by the column of contrast media 30 in outlet 18.

As will be appreciated by those skilled in the art, a variety of types and configurations of seat and float assemblies can be provided without departing from the scope and spirit of the present invention. In one embodiment, the float is disk-shaped and the seat accommodates the disk-shaped float. In another embodiment, the seat includes a plurality of fluid passageways to allow the passage of fluid underneath the float in addition to projections. In another embodiment, projections are provided solely in connection with the seat and are not positioned on the interior of the burette.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A flow regulator assembly for use with a fluid delivery system, the flow regulator assembly comprising:
   a fluid conduit operably coupled to a source of fluid, the fluid conduit allowing the passage of fluid from the source of fluid to a destination of the fluid;
   a seal housing operably linked to the fluid conduit, the seal housing coupled to a burette utilized with the fluid delivery system;
   a vent seal seat positioned within the seal housing;
   a vent seal disposed within the vent seal seat;
   a boundary forming a fluid barrier along at least a portion of a perimeter of the vent seal; and
   a movable member operably linked to the seal housing allowing the user to open and close the flow regulator assembly by causing a deformation in the vent seal along at least a portion of the boundary, such that the user can control the flow of fluid from the source of fluid to the burette and such that the vent seal remains in the vent seal seat when the flow regulator assembly is open and closed.

2. The flow regulator assembly of claim 1, wherein the vent seal comprises a valve.

3. The flow regulator assembly of claim 1, wherein the vent seal comprises a resilient member.

4. The flow regulator assembly of claim 1, wherein the moveable member is manipulated by the user to open the flow regulator assembly.

5. The flow regulator assembly of claim 4, wherein the flow regulator assembly is normally closed and the user manipulates the moveable member to open the flow regulator assembly.

6. The flow regulator assembly of claim 5, wherein the moveable member is configured such that when the user releases the moveable member, the flow regulator assembly automatically closes.

7. The flow regulator assembly of claim 1, wherein opening the flow regulator assembly indirectly allows the flow of fluid.

8. The flow regulator assembly of claim 1, wherein opening the flow regulator assembly directly allows the flow of fluid.

9. A flow regulator assembly for use with a fluid delivery system to control the flow of fluid, the flow regulator assembly comprising:
   a valve comprising:
      a seal housing,
      a disk-shaped vent seal, and
      a boundary forming a fluid barrier along at least a portion of a perimeter of the vent seal;
   a movable member positioned such that a user can exert rotational force on the movable member to selectively open the valve by deforming the vent seal along at least a portion of the boundary to allow the flow of fluid, the movable member being configured such that when the user is no longer exerting rotational force on the movable member, the movable member automatically returns to a position in which the vent seal is closed.

10. The flow regulator assembly of claim 1, wherein the deformation of the vent seal permits passage of fluid in proximity to the deformation.

11. A flow regulator assembly for use with a fluid delivery system, the flow regulator assembly comprising:

a liquid conduit coupled to a source of liquid, the liquid conduit conducting liquid from the source of liquid to a burette;
a seal housing coupled to the burette;
a vent seal seat disposed within the seal housing;
a vent seal positioned within the vent seal seat;
a boundary forming a fluid barrier along at least a portion of a perimeter of the vent seal; and
a movable member configured to open the vent seal by contacting the boundary and causing a deformation of the vent seal within the vent seal seat along at least a portion of the boundary.

12. The flow regulator assembly of claim 11, wherein the vent seal is configured to control passage of air from the burette.

13. The flow regulator assembly of claim 11, wherein the vent seal is configured to control passage of liquid from the liquid conduit into the burette.

14. The flow regulator assembly of claim 11, wherein the boundary is at least partially defined by the seal housing and the perimeter of the vent seal.

15. The flow regulator assembly of claim 14, wherein the deformation of the vent seal causes a separation between the vent seal and the seal housing.

16. The flow regulator assembly of claim 14, wherein the boundary is at least partially defined by the flow regulator assembly and the perimeter of the vent seal.

17. The flow regulator assembly of claim 14, wherein the deformation of the vent seal permits passage of fluid in proximity to the deformation.

* * * * *